United States Patent
Küpper

(10) Patent No.: US 6,813,518 B2
(45) Date of Patent: Nov. 2, 2004

(54) METHOD AND SYSTEM FOR TERMINATING ATRIAL FIBRILLATION BY INDUCING A VENTRICULAR EXTRA-SYSTOLE WITH COMBIPOLAR PACING

(75) Inventor: Bernhard C. H. Küpper, Düsseldorf (DE)

(73) Assignee: Medtronic, Inc., Minneapolis, MN (US)

( * ) Notice: Subject to any disclaimer, the term of this patent is extended or adjusted under 35 U.S.C. 154(b) by 252 days.

(21) Appl. No.: 09/846,769

(22) Filed: Apr. 30, 2001

(65) Prior Publication Data

US 2003/0032986 A1 Feb. 13, 2003

(51) Int. Cl.[7] .............................................. A61N 1/368
(52) U.S. Cl. ........................................ 607/14; 607/15
(58) Field of Search ................. 607/14, 9, 15, 607/4, 59

(56) References Cited

U.S. PATENT DOCUMENTS

| | | | |
|---|---|---|---|
| 5,562,708 A | 10/1996 | Combs et al. | |
| 5,674,251 A | 10/1997 | Combs et al. | |
| 5,683,429 A | 11/1997 | Mehra | |
| 5,871,507 A | 2/1999 | Obel et al. | |
| 6,246,906 B1 * | 6/2001 | Hsu et al. | 607/4 |
| 6,345,198 B1 * | 2/2002 | Mouchawar et al. | 607/4 |
| 6,484,057 B2 * | 11/2002 | Ideker et al. | 607/14 |
| 6,539,260 B1 * | 3/2003 | Schloss | 607/9 |

OTHER PUBLICATIONS

An article from Stimocoeur Medical entitled "Les stimulateurs cardiaques destines a traiter les tachycardies paroxystiques" [Authors Leclercq et al, Tome 7—N° 1—1979, pp. 8–15].

* cited by examiner

Primary Examiner—Kennedy Schaetzle
(74) Attorney, Agent, or Firm—Girma Wolde-Michael; Michael C. Soldner; Thomas F. Woods

(57) ABSTRACT

A method and system for pacing cardiac tissue is provided. Atrial fibrillation is detected in the cardiac tissue. An area of the cardiac tissue is paced with at least one atrial electrode and simultaneously paced with at least one ventricular electrode. A ventricular extra-systole is induced, thereby terminating the atrial fibrillation.

11 Claims, 10 Drawing Sheets

METHOD AND SYSTEM FOR TERMINATING ATRIAL FIBRILLATION BY INDUCING A VENTRICULAR EXTRA-SYSTOLE WITH COMBIPOLAR PACING

FIELD OF THE INVENTION

The present invention relates to the field of implantable medical devices. More particularly, the present invention relates to cardiac pacing systems that provide a method for using pacing pulses to terminate an atrial fibrillation by inducing a ventricular extra-systole through combipolar pacing.

BACKGROUND OF THE INVENTION

Tachyarrhythmias are episodes of high-rate cardiac depolarizations. Tachyarrhythmias may occur in one chamber of the heart or may be propagated from one chamber to another. Some tachyarrhythmias are sufficiently high in rate to compromise cardiac output from the chamber(s) affected, leading to loss consciousness or death, in the case of ventricular fibrillation or weakness and dizziness in the case of atrial fibrillation. Atrial fibrillation is often debilitating, due to the loss of atrial cardiac output, and may sometimes lead to ventricular fibrillation.

Generally, fibrillation may be terminated by administering high energy level cardioversion/defibrillation shocks or pulses until the fibrillation is terminated. For example, in the context of implantable anti-arrhythmia devices, these pulses may be applied by means of large surface area electrodes on or in the chamber to be defibrillated. However, the high energy level pulses are often sufficient to cause pain to the patient. Thus, it would be desirable to prevent or decrease the occurrence of atrial fibrillation.

Thus, some exploration has been made in the use of pacing level pulses, which stimulate the cardiac tissue at much lower levels than defibrillation pulses, to terminate atrial fibrillation. Implantable pulse generators (IPGs) that deliver pacing level pulses are well known in the art. These IPGs may deliver pulses to one or more chambers of the heart. However, in many cases, the low level pacing pulses are not sufficient to terminate atrial fibrillation.

Some exploration has also been made into the possibilities of using ventricular extra-systoles (also known as premature ventricular contractions or PVCs) to capture the atrium and terminate atrial fibrillation.

Some IPGs are dual-chamber, having both atrial and ventricular leads, while other IPGs are multiple-chamber, having one or more leads in two or more chambers of the heart. Such dual-chamber or multiple chamber IPGs have one or more unipolar or bipolar leads in the ventricle and one or more unipolar or bipolar leads in the atrium of the right and/or the left side of the heart. Sensing of cardiac activity takes place either between a tip and a ring of one or more electrodes in a given chamber or between the tip of one or more electrodes in a given chamber and the can of the IPG. Another type of sensing, sometimes called as "combipolar" sensing, takes place between the respective tip electrodes of these unipolar or bipolar leads.

The pacing pulses delivered from such dual-chamber leads and multiple-chamber IPGs may be too low in energy to serve as defibrillation pulses.

However, these IPGs may also pace atrial cardiac tissue with the atrial lead and may pace ventricular tissue with the ventricular lead. The leads of a dual-chamber or a multiple-chamber IPG may also pace tissue between the leads and thereby deliver energy to the ventricle to induce a ventricular extra-systole (VES), also called a premature ventricular contraction (PVC). This type of pacing may simultaneously delivery enough energy to the atria to induce atrial depolarization in the same instance as the VES is being induced.

The close coupling of the premature ventricular action induced by the combipolar pulse to the start of an atrial arrhythmia may induce a rise in atrial pressure. This rise further results in a higher wall tension in the atria thus causing an electrical situation whereas the delivery of energy is more likely to capture the highest possible number of atrial cells. Additionally, the pacing pulses that result from such combipolar pacing may have a higher amplitude and/or pulse width than the usual pacing pulses.

Thus, a need exists in the medical arts for use of combipolar pacing of cardiac tissue to induce a ventricular extra-systole in order to simultaneously terminate atrial fibrillation of the cardiac tissue.

Some methods have been proposed in the prior art for administering pacing pulses to cardiac tissue in order to terminate atrial fibrillation.

For example, U.S. Pat. Nos. 5,562,708 and 5,674,251, both to Combs et al., disclose a pacemaker system adapted to deliver pacing pulses in the presence of fibrillation. An extended pulse train is delivered in order to gradually entrain greater portions of heart tissue, until a sufficient percentage of tissue is entrained to interrupt fibrillation.

U.S. Pat. No. 5,683,429 to Mehra discloses a method and apparatus for preventing fibrillation by distributing sense electrodes one or both atrial chambers. The sense electrodes may be used to sense an atrial premature beat and then to distribute a pacing energy pulse burst simultaneously.

The article "Les stimulateurs cardiaques destinés à traiter les tachycardies paroxystiques" (Cardiac stimulators for treating paroxysmal tachycardias)" in the journal *Stimucoeur Medical* by J. F. Leclercq et al. discloses the use of a pacemaker stimulating an atria and a ventricle simultaneously to terminate an arrhythmia in the case of drug-resistant paroxysmal reciprocating tachycardia.

Some methods have also been proposed in the prior art for combipolar sensing. For example, U.S. Pat. No. 5,871,507 to Obel, et al. discloses the use of signal morphology analysis to detect signals between unipolar atrial and ventricular leads.

The most pertinent prior art patents and publications known at the present time are shown in the following table:

TABLE 1

Prior Art Publications

| U.S. Pat. No. | Date | Inventor(s) |
| --- | --- | --- |
| 5,562,708 | Oct. 8, 1996 | Combs et al. |
| 5,674,251 | Oct. 7, 1997 | Combs et al. |
| 5,683,429 | Nov. 4, 1997 | Mehra |
| 5,871,507 | Feb. 16, 1999 | Obel et al. |

J. F. Leclercq, et al. (1979) "Les stimulateurs cardiaques destinés à traiter les tachycardies paroxystiques" (Cardiac stimulators for treating paroxysmal tachycardias)", *Stimucoeur Medical,* Volume 7, No.1, pp. 8–15.

The publications listed in Table 1 are hereby incorporated by reference herein, each in its entirety. As those of ordinary skill in the art will appreciate readily upon reading the Summary of the Invention, the Detailed Description of the Preferred Embodiments and the Claims set forth below, at least some of the devices and methods disclosed in the patent of Table 1 may be modified advantageously in accordance with the teachings of the present invention.

SUMMARY OF THE INVENTION

The present invention is therefore directed to providing a method and system for terminating atrial fibrillation by inducing a ventricular extra-systole through combipolar pacing. The system of the present invention overcomes at least some of the problems, disadvantages and limitations of the prior art described above, and provides a more efficient and accurate means of terminating atrial fibrillation by inducing a ventricular extra-systole.

The present invention has certain objects. That is, various embodiments of the present invention provide solutions to one or more problems existing in the prior art respecting the pacing of cardiac tissue. Those problems include, without limitation: (a) patients experiencing discomfort while treatment for atrial fibrillation is being administered; (b) atrial fibrillation being terminated using energy pulses which are uncomfortably high or excessive; (c) pacing energy pulses being less effective in the termination of atrial fibrillation than desired; (d) difficulty in administering high energy stimulus pulses to treat atrial fibrillation, and (e) difficulty in providing pacing pulses of sufficient amplitude and pulse width to cause atrial depolarization.

In comparison to known pacing techniques, various embodiments of the present invention provide one or more of the following advantages: (a) the use of pacing energy level pulses, rather than high energy pulse shocks, to treat atrial fibrillation; (b) the ability to create pacing pulses of higher amplitude or pulse width, and (c) fewer patient complaints of discomfort in the treatment of fibrillation.

Some embodiments of the present invention include one or more of the following features: (a) an IPG capable of treating atrial fibrillation by inducing ventricular extra-systole; (b) an IPG capable of delivering pacing energy level pulses of a higher amplitude or pulse width; (c) methods of treating atrial fibrillation with pacing energy level pulses rather than high energy shocks and (d) methods of inducing ventricular extra-systole sufficient to terminate atrial fibrillation without causing distress to the patient.

At least some embodiments of the present invention involve detecting atrial fibrillation in the cardiac tissue. Immediately following detection of atrial fibrillation, an area of the ventricle is simultaneously paced so that at least one pacing pulse is delivered to an area of the ventricle simultaneously from at least one atrial electrode and at least one ventricular electrode. This simultaneous combipolar pacing induces a ventricular extra-systole for the duration in order to terminate the atrial fibrillation. After the duration ends, the occurrence of atrial fibrillation is again measured. If atrial fibrillation is still detected, another combipolar pacing pulse is administered.

The ventricular extra-systole may be sensed. The simultaneous pacing may occur for a duration, which may be determined using any suitable means. The cardiac tissue may also be placed at a regular function once the duration is over. The rates of pacing with the at least one atrial electrode and/or the at least one ventricular electrode may be adjusted. Simultaneous, combipolar pacing of the area of cardiac tissue may be stopped once the ventricular extra-systole has been delivered and redetection of the atrial rhythm shows a regular function.

BRIEF DESCRIPTION OF THE DRAWINGS

The above, and other objects, advantages and features of the present invention will be more readily understood from the following detailed description of the preferred embodiments when considered in conjunction with the drawings, in which like reference numerals indicate identical structures throughout the several views, and wherein.

DETAILED DESCRIPTION OF THE PRESENTLY PREFERRED EMBODIMENTS

It is to be understood that the terms "IPG" and "IMD", as employed in the specification and claims hereof, means an implantable medical device capable of delivering electrical stimuli to cardiac tissue, and includes within its scope pacemakers, PCDs, ICDs, etc.

Figure 1:
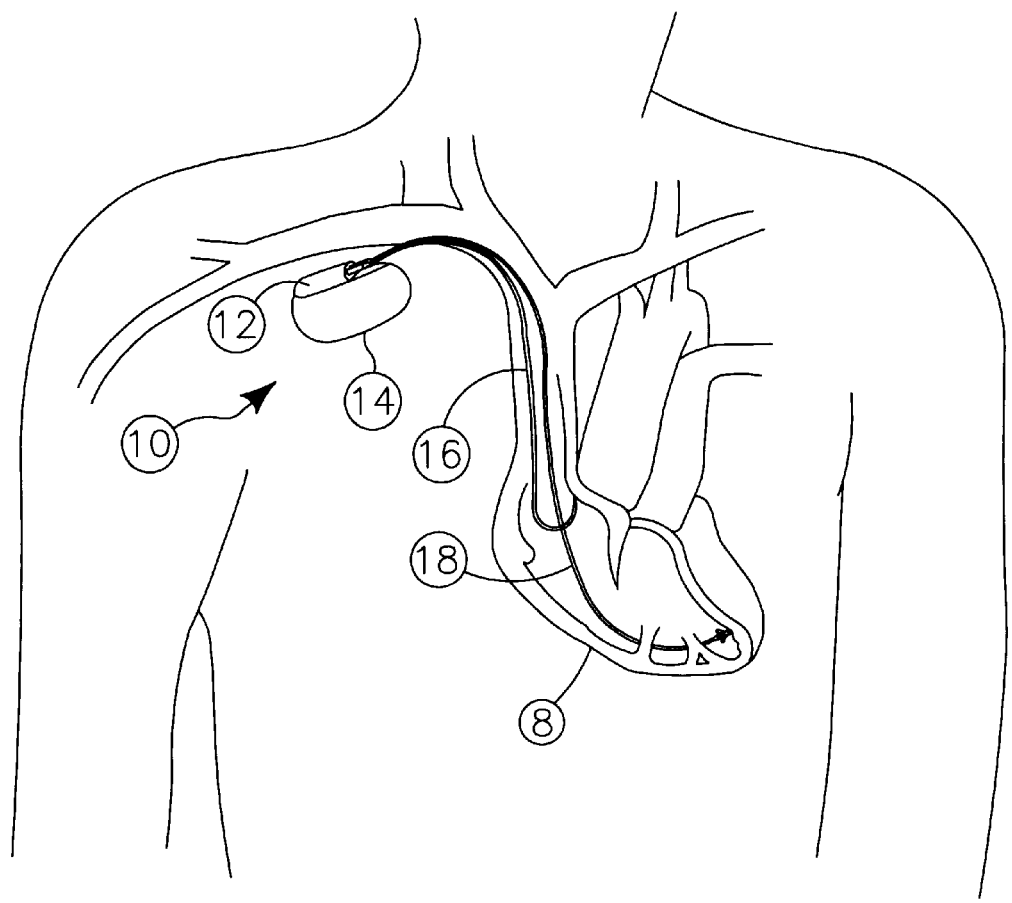
FIG. 1 is a schematic view of one embodiment of an implantable medical device in situ, made in accordance with the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. In one embodiment of the invention, leads 16 and 18 are adapted to administer combipolar pacing pulses to cardiac tissue. For example, lead 16 may be adapted to administer pacing pulses as an atrial lead and lead 18 may be adapted to administer pacing pulses as a ventricular lead, or vice versa. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference herein, each in its respective entirety.

Figure 2:
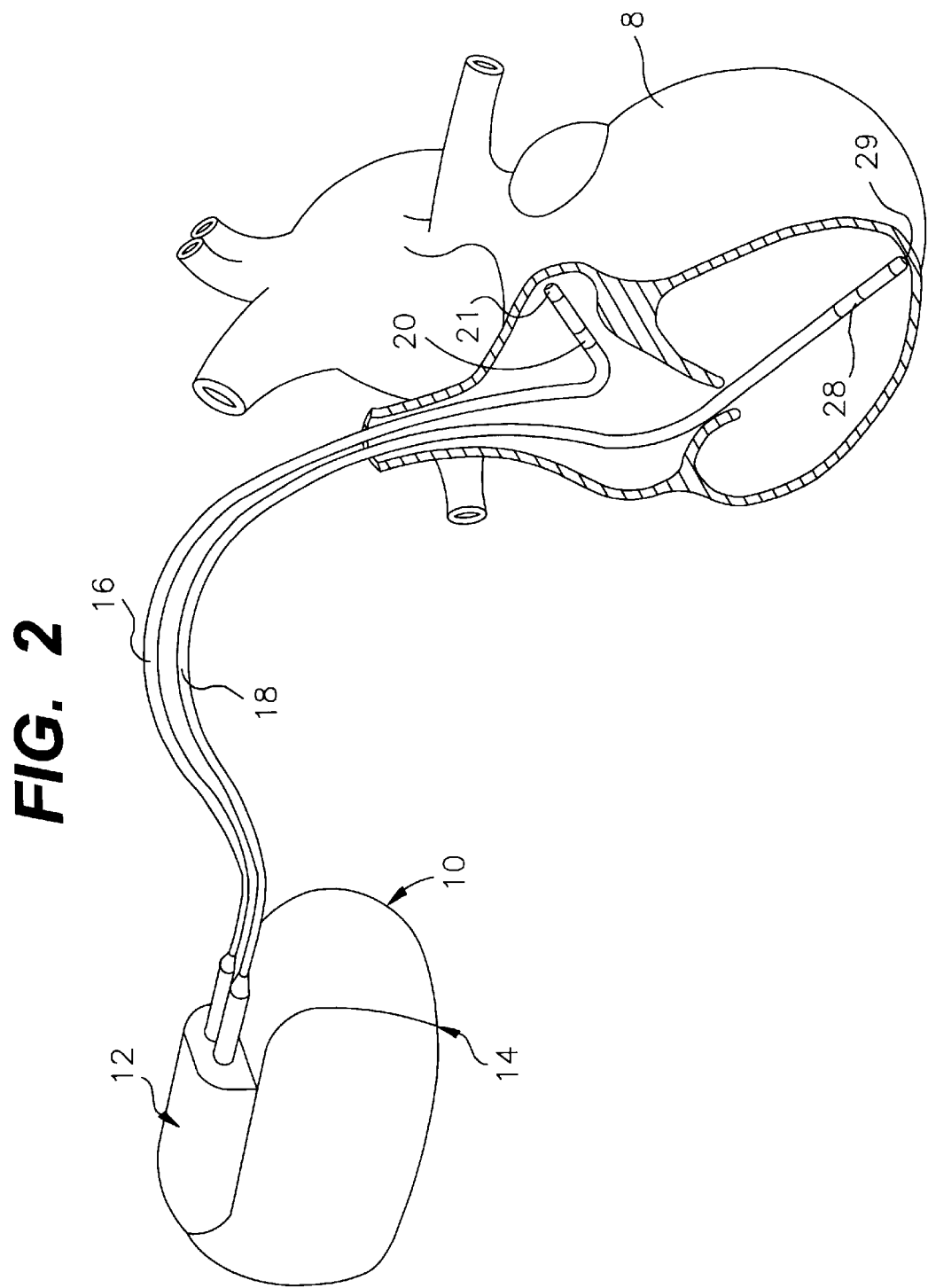
FIG. 2 is another schematic view of an embodiment of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
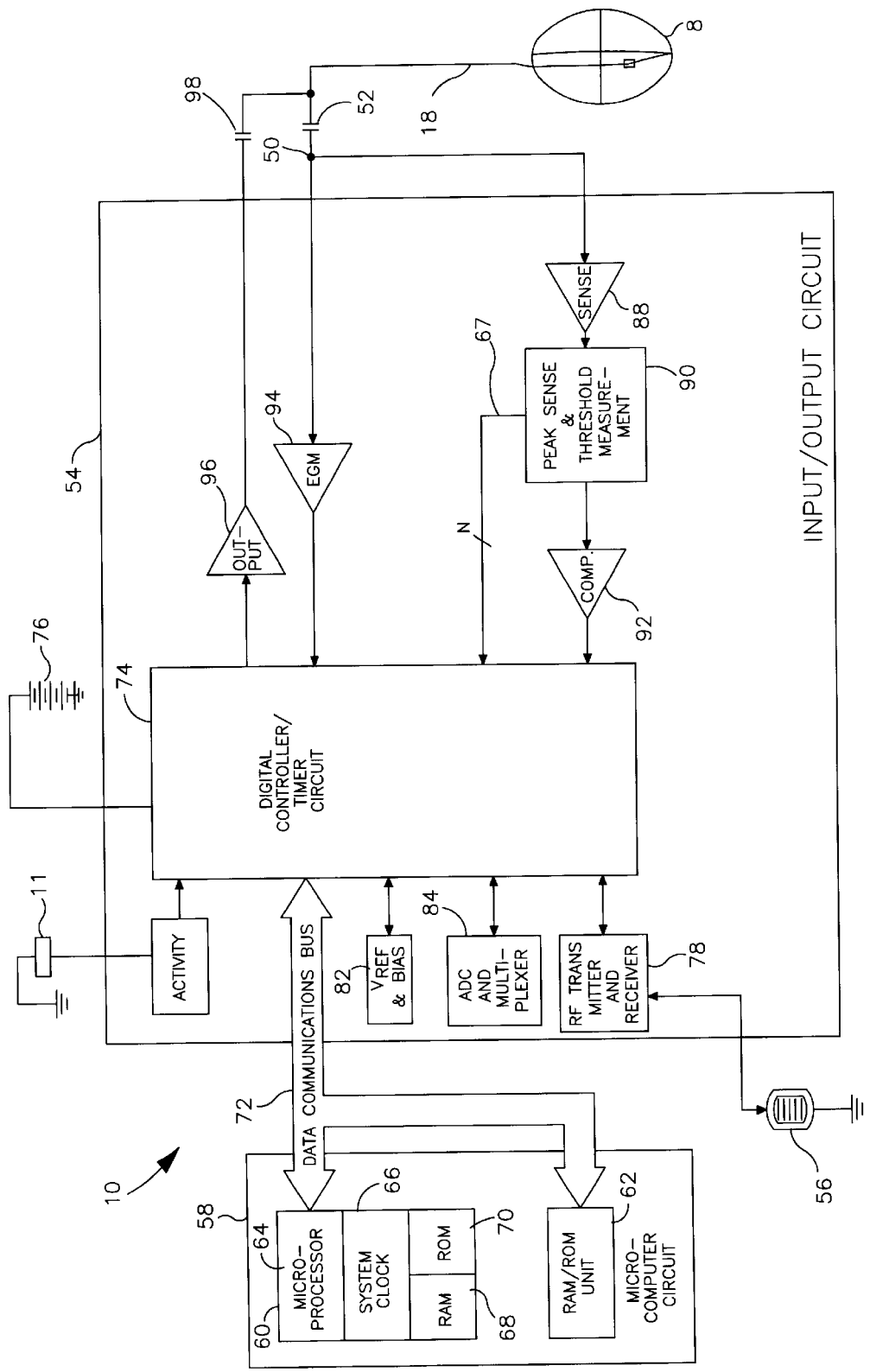
FIG. 3 is a block diagram illustrating components of an embodiment of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which may be an accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 may be programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in U.S. Pat. No. 5,312,453 to Wyborny et al. is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 may be attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. Accordingly, the rate at which heart 8 is stimulated or beats spontaneously without stimulation may be controlled and/or monitored using software-implemented algorithms or pacing rate functions stored in microcomputer circuit 58. In one embodiment of the invention, the stimulating pulses are applied in a combipolar pacing fashion, in which pacing occurs between the atrial and ventricular leads.

Microcomputer circuit 58 may comprise on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 may include microprocessor 64, system clock circuit 66 and on-board RAM 68 and ROM 70. Off-board circuit 62 may comprise a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 may generate stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 may be coupled to sensing circuitry, including sense amplifier 88, peak sense and threshold measurement unit 90 and comparator/threshold detector 92. Circuit 74 may further be coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. In one embodiment of the invention, IMD 10 is capable of operating in response to the sensing of atrial fibrillation in order to terminate the fibrillation. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMDs comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMDs. One embodiment of the invention is applied in the context of a dual-chamber pacemaker with at least one atrial least and at least one ventricular lead. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCDs. Various embodiments of the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference herein, each in its respective entirety.

Figure 4:
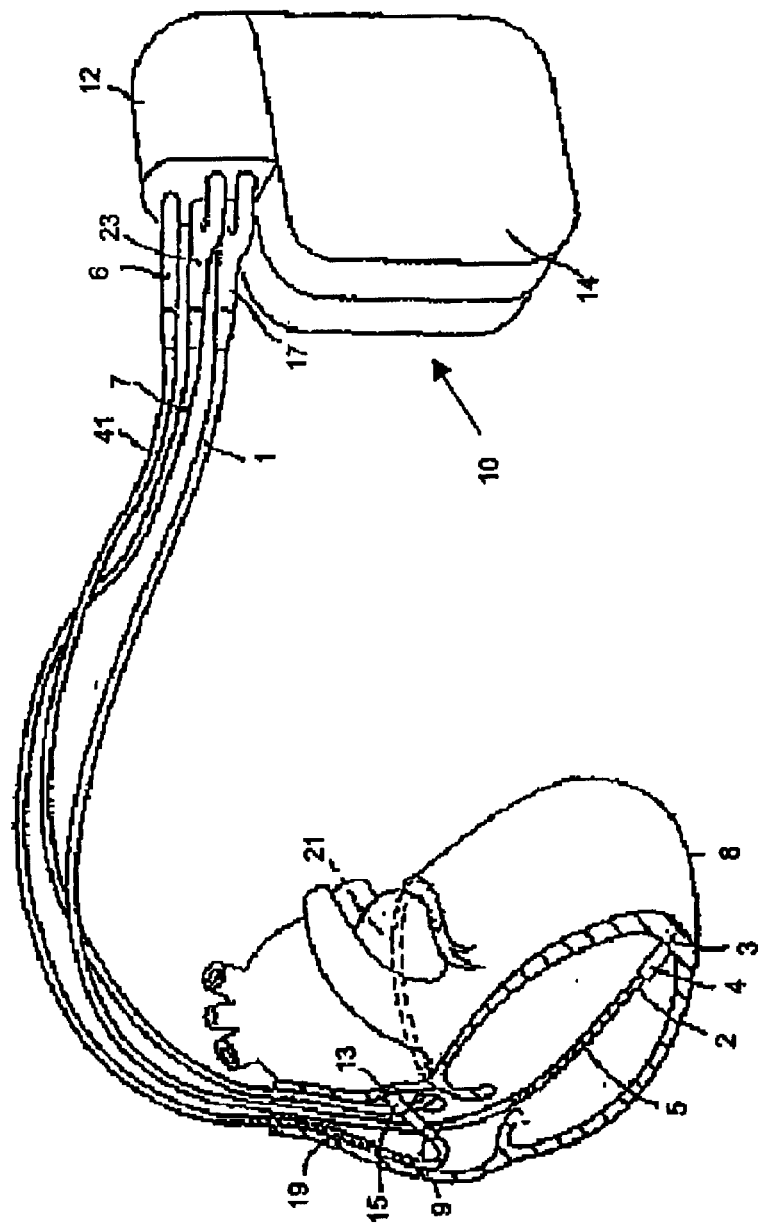
FIG. 4 is a schematic view of another embodiment of an implantable medical device, made in accordance with the present invention.
Figure 5:
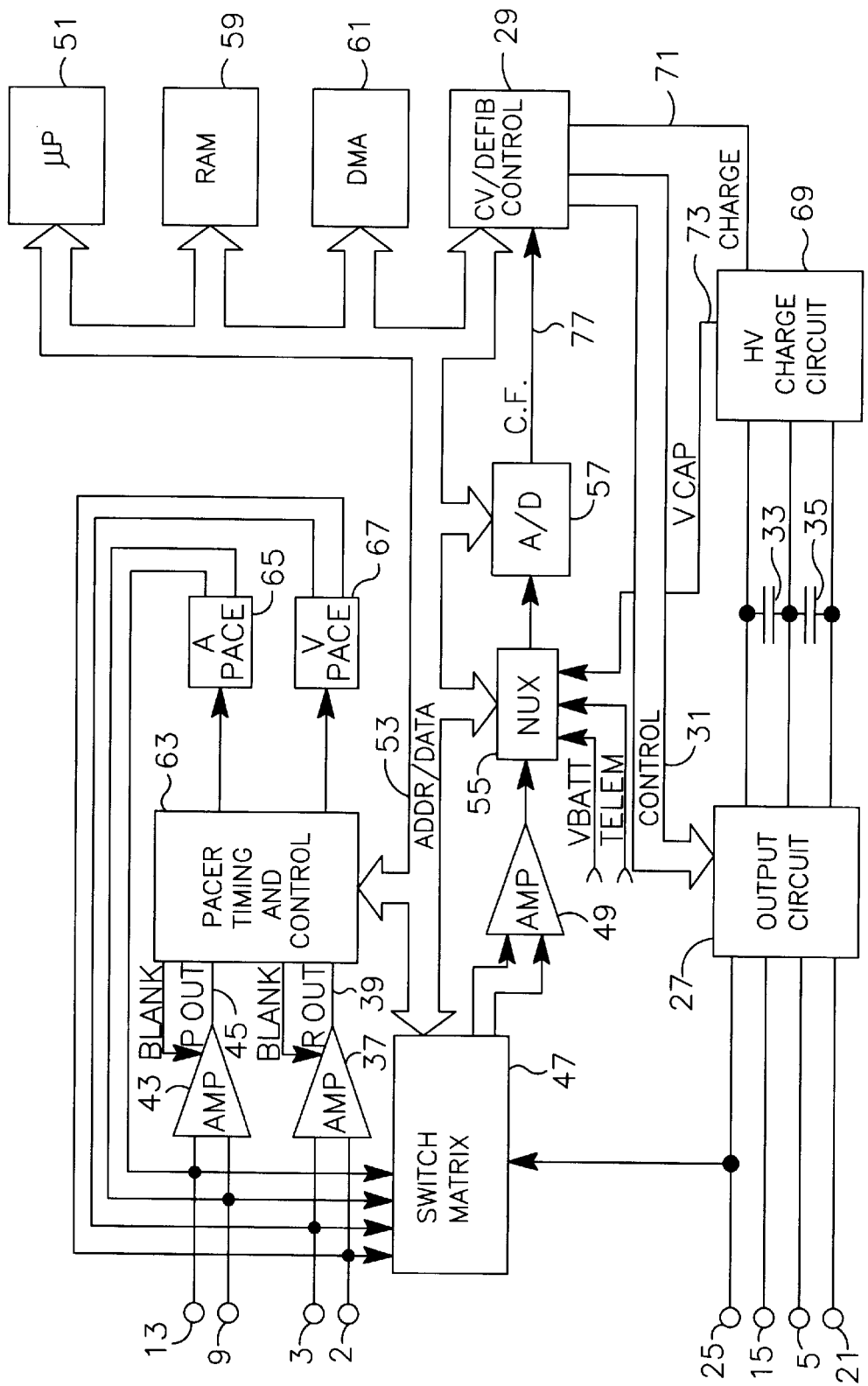
FIG. 5 is a block diagram illustrating components of an embodiment of the implantable medical device of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 7 carrying three concentric coiled conductors separated from one another by tubular insulative sheaths. Located adjacent the distal end of lead 7 are ring electrode 2, extendable helix electrode 3 mounted retractably within insulative electrode head 4 and elongated coil electrode 5. Each of the electrodes is coupled to one of the coiled conductors within lead body 7. Electrodes 2 and 3 may be employed for cardiac pacing and for sensing ventricular depolarizations. Electrodes 2 and 3 may also be employed for administering combipolar pacing pulses in order to induce a ventricular extra-systole.

At the proximal end of the lead is bifurcated connector 17, which carries three electrical connectors, each coupled to one of the coiled conductors. Defibrillation electrode 5 may be fabricated from platinum, platinum alloy or other materials known to be usable in implantable defibrillation electrodes and may be about 5 cm in length. In one embodiment of the invention, defibrillation electrodes 5 may be used to aid in the administration of stimulating pulses to induce a ventricular extra-systole.

The atrial/SVC lead shown in FIG. 4 includes elongated insulative lead body 41 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 41. Electrodes 13 and 9 may be employed for atrial pacing and for sensing atrial depolarizations. Electrodes 9 and 13 may also be employed for administering combipolar pacing pulses in order to induce a ventricular extra-systole. Elongated coil electrode 19 is provided proximal to electrode 9 and coupled to the third conductor within lead body 41. In one embodiment of the invention, electrode 19 is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 23, which carries three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 1 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 6 carrying an electrical connector coupled to the coiled conductor. The coronary sinus/great vein electrode 21 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other than those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which may take the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold. In one embodiment of the invention, at least one of electrodes 2, 3 is used in a combipolar pacing fashion to induce a ventricular extrasystole in conjunction with one of the atrial electrodes described below.

Electrodes 9 and 13 are located on or in the atrium and are coupled to the P-wave amplifier 43, which may also take the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety. In one embodiment of the invention, at least one of electrodes 9 or 13 is used in a combipolar pacing fashion to induce a ventricular extrasystole in conjunction with one of the ventricular electrodes described above.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 may include programmable digital counters which control the basic time intervals associated with DDD, VVI, DVI, VDD, AAI, DDI and other modes of single and dual chamber pacing well known to the art. Circuitry 63 also may control escape intervals associated with anti-tachyarrhythmia pacing in both the atrium and the ventricle, employing any anti-tachyarrhythmia pacing therapies known to the art. Circuitry 63 may also be used to administer combipolar pacing in accordance with the present invention.

Intervals defined by pacing circuitry 63 include atrial and ventricular pacing escape intervals, the refractory periods during which sensed P-waves and R-waves are ineffective to restart timing of the escape intervals and the pulse widths of the pacing pulses and combipolar pacing escape intervals. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51. Pacer circuitry 63 may also determine the amplitude of the combipolar pacing pulses administered under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 may operate as an interrupt driven device, and may be responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are hereby incorporated by reference herein, each in its respective entirety.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated herein by reference, each in its respective entirety, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to a cardiac pacing mode and awaits the next successive interrupt due to pacing or the occurrence of a sensed atrial or ventricular depolarization.

Alternatively, microprocessor 51 may employ an escape interval counter to control timing of combipolar pacing pulses between an atrial and a ventricular lead, such as leads 16 and 18, respectively, as well as associated refractory periods. In response to the detection of atrial or ventricular fibrillation or tachyarrhythmia requiring stimulation to terminate fibrillation, microprocessor 51 activates combipolar pacing control circuitry (which may be part of circuitry 63). The atrial lead and the ventricular lead then pace the tissue between them. This creates a field, which induces a ventricular extra-systole. Thereafter, timing of the delivery of the combipolar pacing pulse is controlled by pacer timing/control circuitry 63. For example, several combipolar pacing pulses may be delivered before a ventricular extra-systole and termination of atrial fibrillation is achieved. Alternatively, the amplitude of the combipolar pacing pulse may be modified in order to achieve the desired ventricular extra-systole. Alternatively, the pulse width of the combipolar pacing pulse may be modified in order to achieve the desired ventricular extra-systole.

Following delivery of the fibrillation or tachycardia therapy, microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all of which are hereby incorporated by reference herein, each in its respective entirety, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches, which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra, and in U.S. Pat. No. 4,727,877, both of which are hereby incorporated by reference herein in its entirety.

An example of circuitry that may be used to control delivery of monophasic pulses is disclosed in U.S. Pat. No. 5,163,427 to Keimel, also hereby incorporated by reference herein in its entirety. Output control circuitry similar to that disclosed in U.S. Pat. No. 4,953,551 to Mehra et al. or U.S. Pat. No. 4,800,883 to Winstrom, both incorporated by reference, each in its respective entirety, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
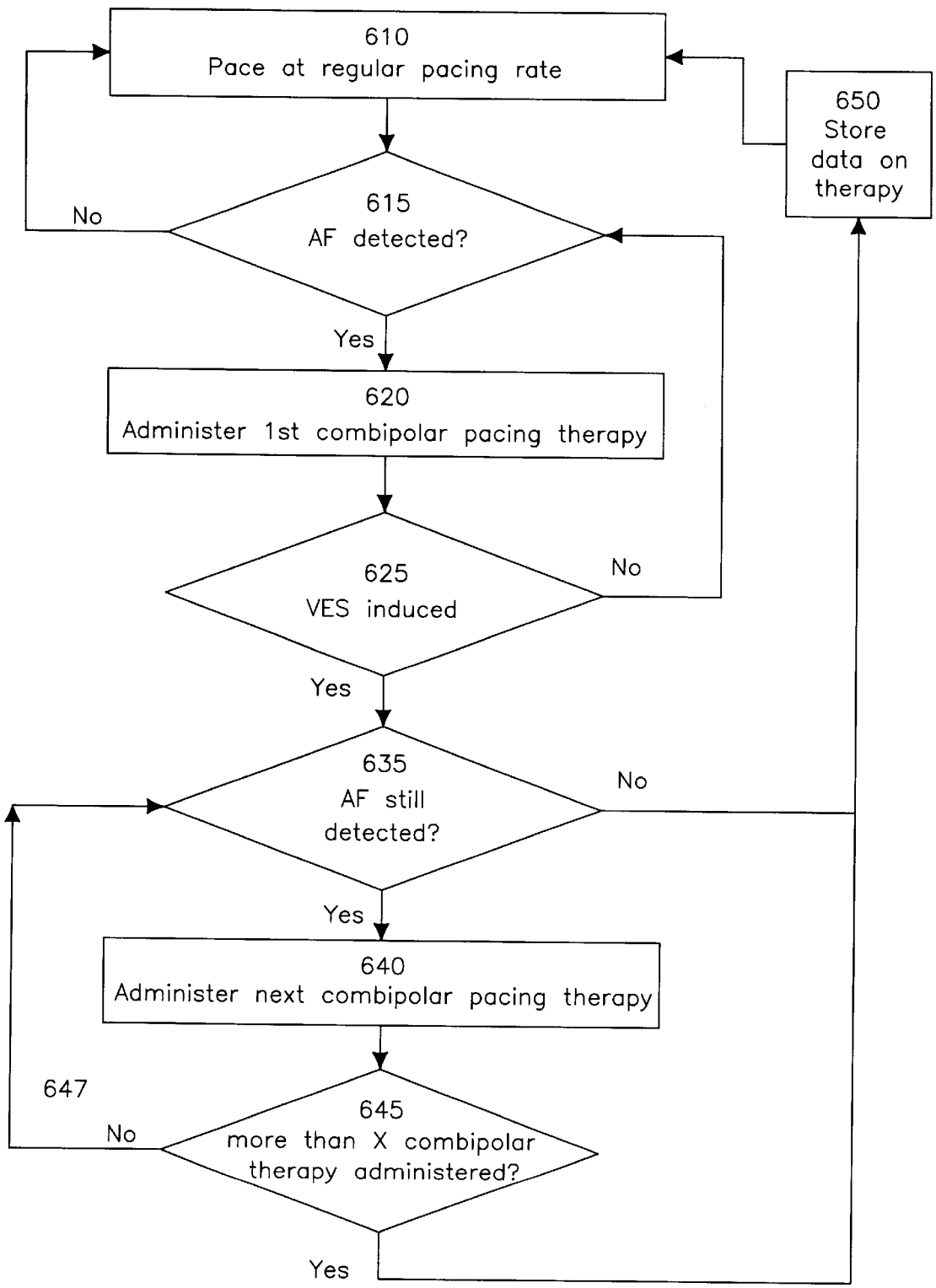
FIG. 6 is a flow diagram of one embodiment of a method for terminating atrial fibrillation in accordance with the present invention.

FIG. 6 illustrates one embodiment of a method for terminating atrial fibrillation in accordance with the present invention. As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

At block 610, the cardiac tissue is paced at a regular pacing function. In one embodiment of the invention, the regular pacing function comprises pacing in a non-combipolar pacing fashion. Regular pacing function may be determined and set by a physician, may be based on the patient's medical history, may be a preprogrammed pacing function, may be selected from a look-up table or database, or calculated based on data gathered by IMD 10. Thus, at block 610, the right atrium may be paced by an electrode located within the right atrium, for example, atrial electrode 9, 13. Alternatively, the left atrium may be paced by an electrode located within the left atrium, for example, atrial electrode 9, 13. Meanwhile, the right ventricle may be paced by an electrode located within the right ventricle, for example, ventricular electrode 2, 3. Alternatively, the left ventricle may be paced by an electrode located within the left ventricle, for example, ventricular electrode 2, 3.

At block 615, it may be determined whether atrial fibrillation is detected. This may be determined using any suitable method known in the arts. For example, the sensing of a premature atrial contraction (PAC) or a premature ventricular contraction (PVC) is known in the art to indicate that atrial fibrillation is occurring. The PAC/PVC may be sensed, for example, by one or more of the sensing leads described above or by activity sensor 11. The occurrence of atrial fibrillation may be determined, for example, by an appropriate computer algorithm stored in memory or a portion of memory of microcomputer 58 of IMD 10. If no atrial fibrillation is detected, the method returns to block 610 and the heart is paced at its regular pacing function. Alternatively, the heart may be paced at any suitable value if no atrial fibrillation occurs.

Figure 8:
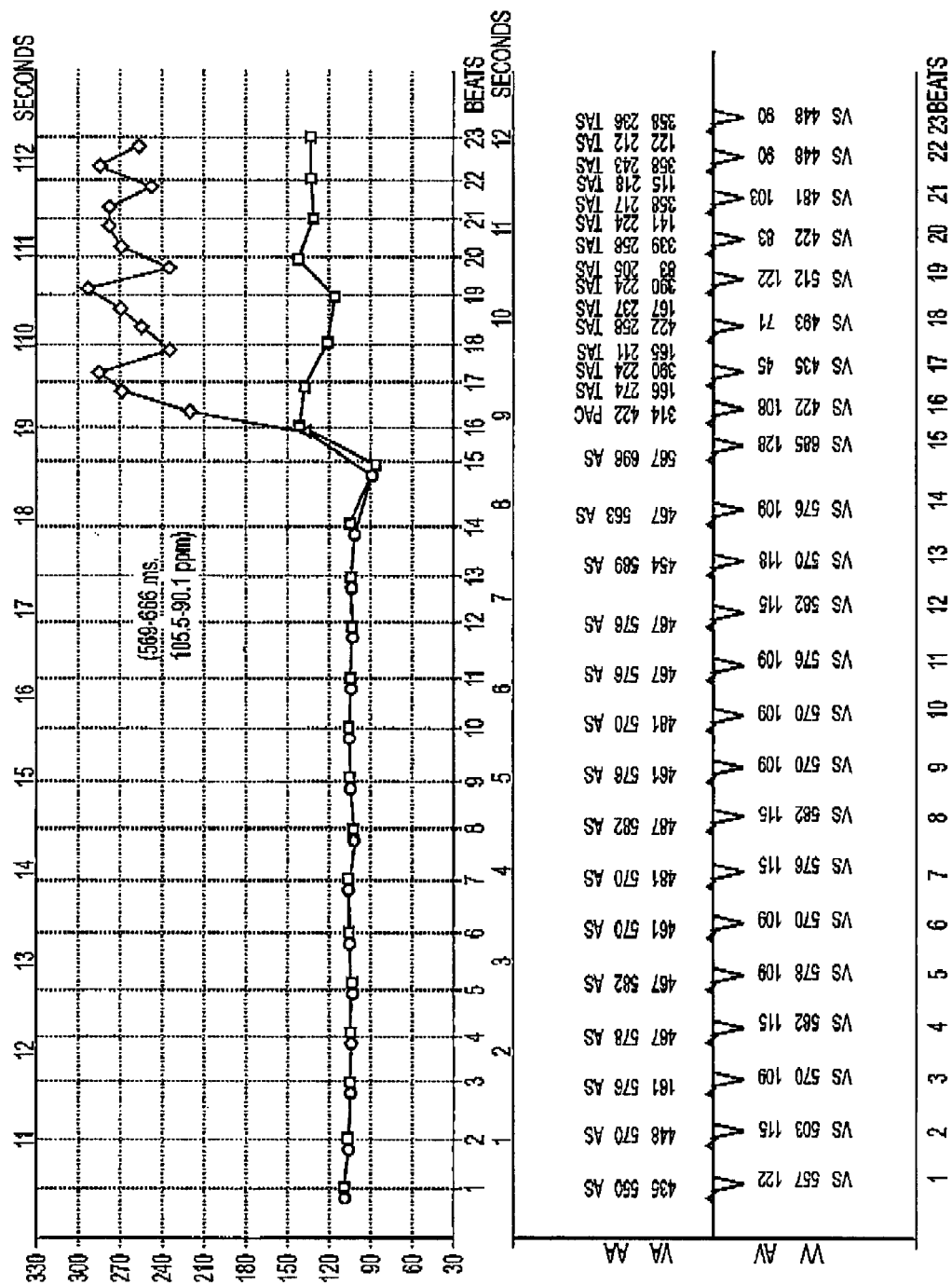
FIGS. 8–10 illustrate examples indicative of the onset of atrial fibrillation.

In one embodiment of the invention, an atrial arrhythmia that may indicate the onset of atrial fibrillation may be detected at block 615. For example, the first beat to start an atrial arrhythmia may succeed the last series of sinus beats by at least 270–280 ms. Thus, the first beat of an atrial arrhythmia will have the defined shortest interval for a given patient. This may be, for example, a PAC. So, in one embodiment of the invention, a given patient may have a minimum interval preprogrammed or predetermined for IMD 10. This shortest interval may be determined and set by a physician, may be based on the patient's medical history, may be a preprogrammed pacing interval, may be selected from a look-up table or database, or calculated based on data gathered by IMD 10. If an interval detected by IMD 10 is less than this shortest interval, atrial fibrillation may have occurred and the method will proceed to block 620. Generally, the drop to this shortest interval is sudden and the interval is markedly shorter than the previous interval. FIG. 8 illustrates one example based on clinical data, of such a sudden drop to the shortest interval, which may be indicative of the onset of atrial fibrillation.

Figure 9:
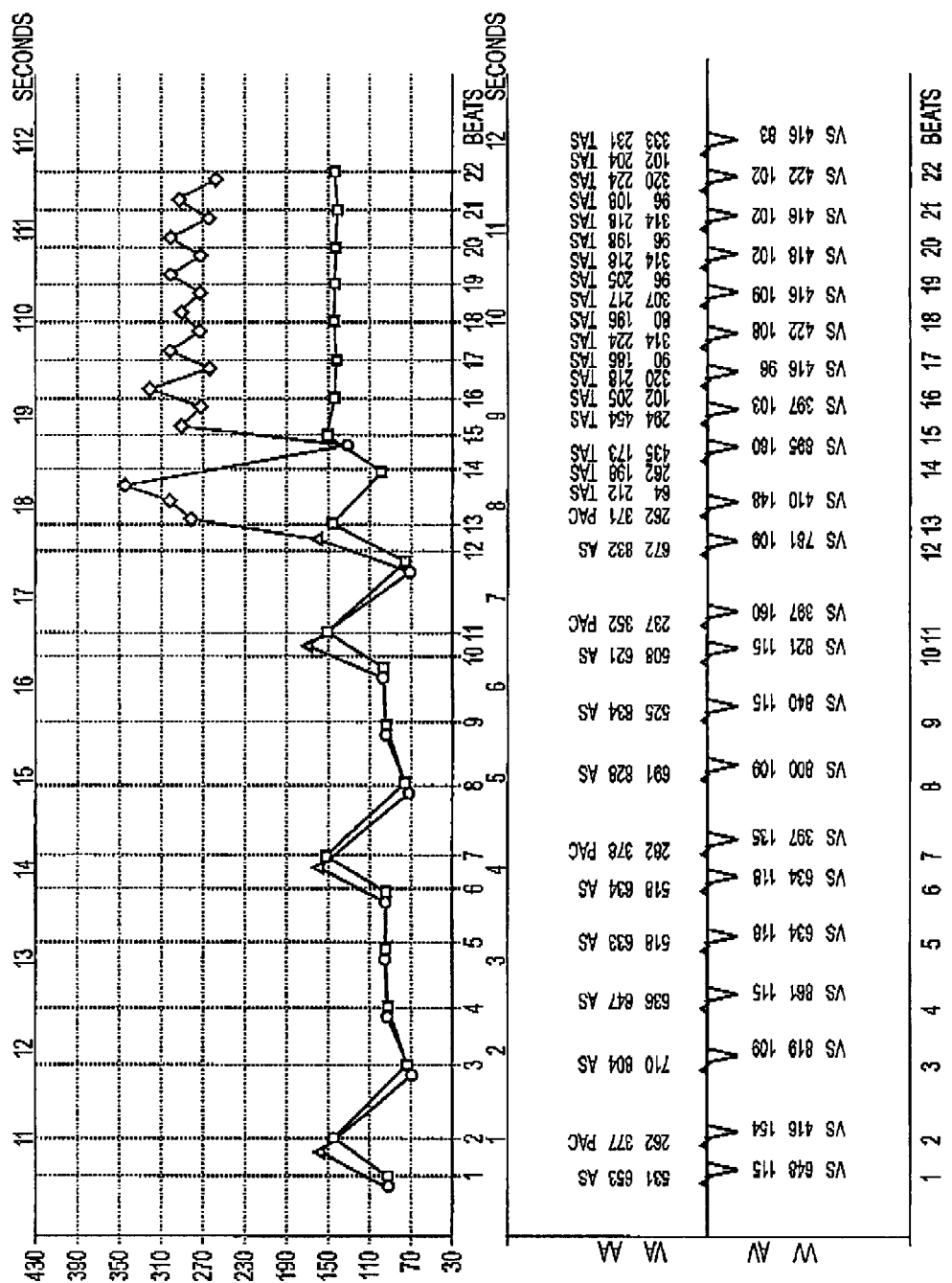

In an alternate embodiment of the invention, a plurality of atrial arrhythmias that may indicate the onset of atrial fibrillation may be detected at block 615. A first beat of an atrial arrhythmia may be detected, for example, because its interval is less than the shortest interval defined for the patient as described above. Then, IMD 10 may evaluate whether at least one more beat of atrial arrhythmia occurs succeeding the first beat detected above. If IMD 10 detects more than one atrial arrhythmia, i.e., a series of atrial arrhythmias, then atrial fibrillation may have occurred and the method will proceed to block 620. In one embodiment of the invention, two detected atrial arrhythmia beats will cause the method to proceed to block 620. Alternatively, three detected atrial arrhythmia beats will cause the method to proceed to block 620. Alternatively, any suitable number of detected beats may be used. For example, FIG. 9 illustrates one example, based on clinical data, of such multiple preceding PACs which may be indicative of the onset of atrial fibrillation. In FIG. 9 four preceding detected atrial arrhythmia beats (four PACs) are shown.

Figure 10:
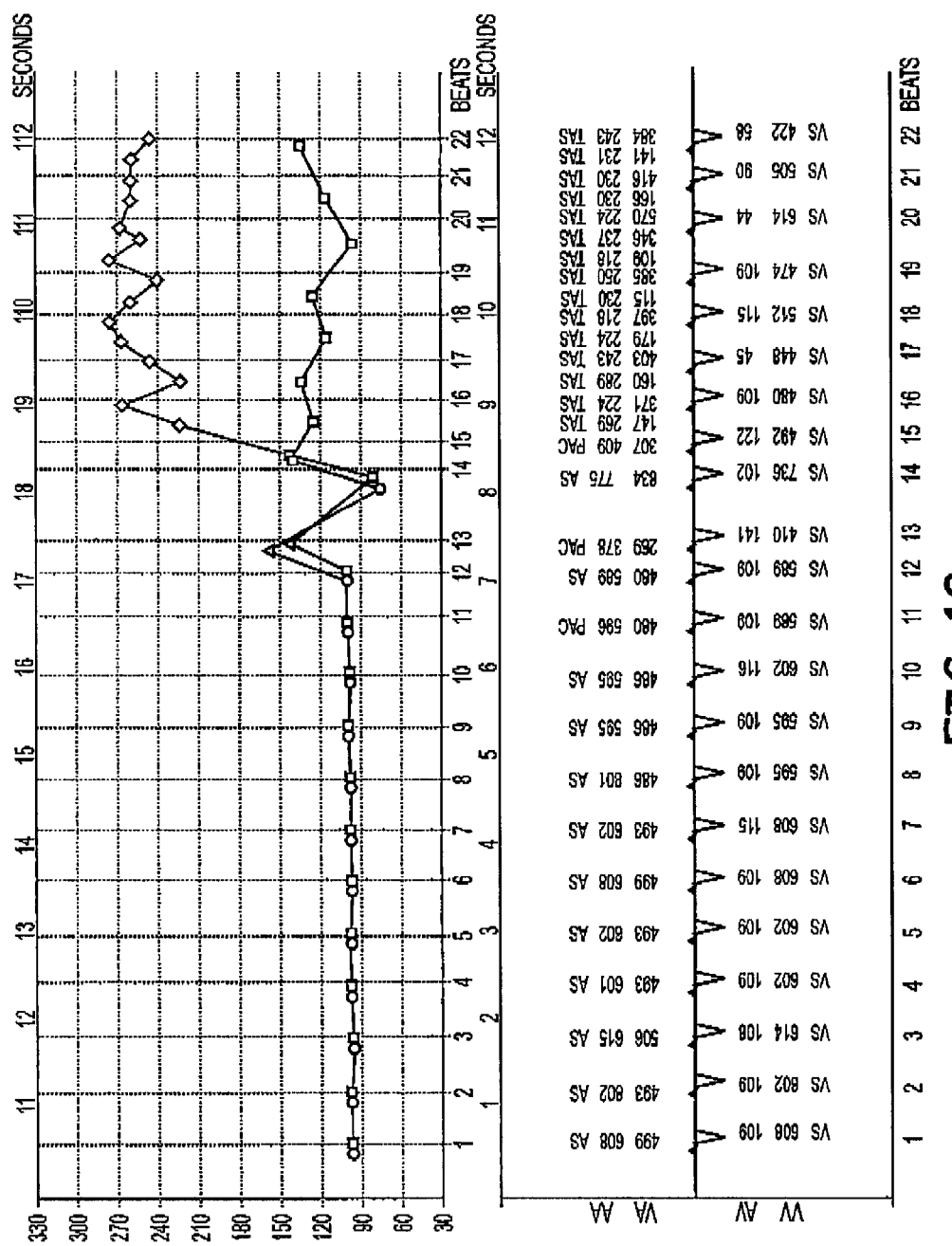

In other embodiments of the invention, IMD 10 may determine the length of the interval between the first detected atrial arrhythmia beat and the beat following the first detected atrial arrhythmia beat and/or the length of the interval between any two subsequent detected beats. The length of this interval may also be compared to the shortest interval determined for the patient. If the determined interval is shorter than the shortest interval and is then followed by a longer interval (sometimes called a post-PAC interval) atrial fibrillation may have occurred and the method will proceed to block 620. In one embodiment of the invention, two detected atrial arrhythmia beats with short intervals may be followed by a longer interval and will also cause the method to proceed to block 620. Alternatively, any combination of detected atrial arrhythmia beats with an interval shorter than the shortest interval determined for the patient followed by a long post-PAC interval will cause the method to proceed to block 620. Alternatively, any interval determined between two of any suitable number of detected beats may be used. For example, FIG. 10 illustrates one example, based on clinical data, of such short-long interval combinations, which may be indicative of the onset of atrial fibrillation.

Thus, atrial arrhythmia may be detected within two to three actions of the first detected atrial arrhythmia beat.

If atrial fibrillation is detected, the method may proceed to block 620, when a first combipolar pacing therapy is delivered to the ventricle. This may take the form of, for example, a single combipolar pacing pulse. Combipolar pacing may be accomplished using any suitable method known in the arts. In one embodiment, leads 16 and 18 described above may be adapted to administer combipolar pacing pulses to cardiac tissue. For example, lead 16 may be adapted to administer pacing pulses as a ventricular lead. Thus, lead 16 and lead 18 may administer a combipolar pulse by pacing at least one of the ventricles simultaneously. In at least some embodiments of the invention, a combipolar pulse may also be delivered in an alternating fashion, for example, the ventricle may be paced with lead 16 and immediately after with lead 18 or with lead 18 followed by lead 16. In some embodiments of the invention, combipolar pacing is preferably administered to the right ventricle. Alternatively a combipolar pacing pulse may be administered to an area of the right ventricle which bypasses right ventricle outflow tracks. Alternatively, a combipolar pacing pulse may be administered to the apex of the right ventricular sinus.

Alternatively, at least one of ventricular electrodes 2, 3 is used in a combipolar pacing fashion to induce a ventricular extra-systole in conjunction with at least one of the atrial electrodes 9, 13. Thus ventricular electrode 2,3 and atrial electrode 9, 13 may administer a combipolar pulse by pacing at least one of the ventricles simultaneously. In at least some embodiments of the invention, a combipolar pulse may also be delivered in an alternating fashion, for example, the ventricle may be paced with ventricular electrode 2,3 and then with atrial electrodes 9, 13 or vice versa, i.e., with atrial electrodes 9, 13 followed by ventricular electrodes 2, 3. In some embodiments of the invention, combipolar pacing is preferably administered to the right ventricle. Alternatively a combipolar pacing pulse may be administered to an area of the right ventricle which bypasses right ventricle outflow tracks. Alternatively, a combipolar pacing pulse may be administered to the apex of the right ventricular sinus.

In another embodiment of the invention ring electrode 2 may be adapted to administer pacing pulses as an atrial lead and coil electrode 5 may be adapted to administer pacing pulses as a ventricular lead, or vice versa. Thus, electrode 2 and electrode 5 may administer a combipolar pulse by pacing at least one of the ventricles simultaneously. In at least some embodiments of the invention, a combipolar pulse may also be delivered in an alternating fashion, for example, the ventricle may be paced with electrode 2 followed by electrode 5 or vice versa, i.e., the ventricle may be paced with electrode 5 followed by electrode 2. In some embodiments of the invention, combipolar pacing is preferably administered to the right ventricle. Alternatively a combipolar pacing pulse may be administered to an area of the right ventricle which bypasses right ventricle outflow tracks. Alternatively, a combipolar pacing pulse may be administered to the apex of the right ventricular sinus.

In one embodiment of the invention, circuitry 63 may be used to administer a combipolar pacing pulse by controlling pulses delivered from one or more electrodes.

The combipolar pacing therapy preferably delivers an effective amount of energy sufficient to terminate atrial fibrillation. The combipolar pacing may create a field in the area between the atrial and the ventricular leads. This field may cause the paces delivered by one or more of the atrial and/or ventricular leads to have a higher than normal amplitude or pulse width. Alternatively, a low energy pulse may be delivered from the combination of atrial and ventricular electrodes. In one embodiment of the invention, each of the electrodes delivers the maximum energy it is capable of delivering during administration of its first combipolar pacing pulse. Alternatively, a combination of low and high energy pulses may be administered as a first combipolar pacing pulse. In one embodiment of the invention, the first combipolar pacing pulse is administered for a duration long enough to cause a ventricular extra-systole. In at least some embodiments of the invention, a ventricular action is initiated after a 600 ms duration. Other possible ranges of duration include, but are not limited to 200 to 1000 ms, 300 to 900 ms, 400 to 800 ms, 500 to 700 ms and 550 to 650 ms.

At block 625, it may be determined if a ventricular extra-systole has been induced. The ventricular extra-systole may be sensed with any of the sensing electrodes described above. In one embodiment of the invention, the ventricular extra-systole is induced by the combipolar pacing of block 620. Detection of a ventricular extra-systole may be accomplished using any suitable method known in the arts. In one embodiment, one or more of sensing leads 16 and 18 and/or activity sensor 11 described above may be adapted to sense a ventricular extra-systole. Alternatively, at least one of ventricular electrodes 2, 3 may sense the ventricular extra-systole. In one embodiment of the invention, circuitry 63 may be used to determine if a ventricular extra-systole has been sensed.

In one embodiment of the invention, the ventricular extra-systole will have a interval shorter than the ordinary ventricular interval of the patient. This ordinary interval may be determined and set by a physician, may be based on the patient's medical history, may be a preprogrammed pacing interval, may be selected from a look-up table or database, or calculated based on data gathered by IMD 10.

In at least some embodiments of the invention, IMD 10 may determine the given interval of the first two or more detected atrial arrhythmia beats and will trigger delivery of the first combipolar pacing therapy so that it is administered on at a point in time which corresponds to the determined interval minus a selectable percentage of the determined interval, i.e., $$\text{time of combipolar pacing interval} = \\ \text{determined interval} - \text{percentage of determined interval}$$

This percentage may be based on the vulnerable phase of the T-wave. The T-wave phase may be sensed, for example using sensor 11 or the sensing electrodes described above. Alternatively, the percentage may be calculated from a programmable dynamic refractory period. This calculation may be accomplished, for example under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

If a not induced ventricular action is detected with the desired predetermined ordinary interval, a ventricular extra-systole may have occurred and the method may proceed to block 635. If a ventricular action is detected with an interval shorter than the predetermined ordinary interval concurrently succeeded by one or more ventricular actions with intervals equal to or shorter than the predetermined ordinary interval, a ventricular-couplet or run may have occurred and the method may proceed to block 635.

At block 635, it may again be determined whether atrial fibrillation is occurring. This may be determined using any suitable method known in the arts. For example, the sensing of a premature atrial contraction (PAC) or a premature ventricular contraction (PVC) is known in the art to indicate that atrial fibrillation is occurring. The PAC/PVC may be sensed, for example, by one or more of the sensing leads described above or by activity sensor 11. The occurrence of atrial fibrillation may be determined, for example, by an appropriate computer algorithm stored in memory or a portion of memory of microcomputer 58 of IMD 10. If atrial fibrillation is no longer detected, the method returns to block 610 and the heart is paced at its regular pacing function. Alternatively, the heart may be paced at any suitable value once atrial fibrillation has been terminated. Before or while the heart returns to ordinary pacing function, data regarding the number of combipolar pacing therapies administered and the efficacy of the therapies administered may be stored for later retrieval and evaluation at block 650. This data may be stored, for example, in a storage location of IMD 10, including but not limited to, a location of memory 59 and/or RAM 68.

At block 635, determination if atrial fibrillation is still occurring may be made using the methods described above and illustrated in FIGS. 8–10, i.e., detecting an atrial arrhythmia that may indicate the onset of atrial fibrillation, detecting an atrial arrhythmia with an interval shorter than an predetermined interval established for the patient, detecting a plurality of atrial arrhythmias, and/or measuring the intervals of a plurality of atrial arrhythmias. In another embodiment of the invention, IMD 10 may redetect the atrium and re-tune to the existing cycle length. IMD 10 may then evaluate whether the existing cycle length represents atrial arrhythmia.

If atrial fibrillation is still detected, the method may proceed to block 640, when a next combipolar pacing therapy is delivered to the ventricle. This make take the form of, for example, a single combipolar pacing pulse. Combipolar pacing may be accomplished using any suitable method known in the arts. Combipolar pacing may be accomplished as described above using leads 16 and 18, ventricular electrodes 2, 3 and atrial electrodes 9, 13, or using ring electrode 2 and coil electrode 5.

In one embodiment of the invention, circuitry 63 may be used to administer a combipolar pacing pulse by controlling pulses delivered from one or more electrodes.

The combipolar pacing therapy preferably delivers an effective amount of energy sufficient to terminate atrial fibrillation. The combipolar pacing may create a field in the area between the atrial and the ventricular leads. In some embodiments of the invention, the field is created by delivering high amplitude energy and using a broad pulse width. Alternatively, a low energy pulse may be delivered from the combination of atrial and ventricular electrodes. In one embodiment of the invention, each of the electrodes delivers the maximum energy it is capable of delivering during administration of the next combipolar pacing pulse. Alternatively, a combination of low and high energy pulses may be administered as the next combipolar pacing pulse. Alternatively, the amount of energy administered may be modified based on the amount of energy delivered with the first combipolar pacing therapy. For example, the next combipolar pacing pulse delivered at block 640 may be of a lower or higher energy than the first combipolar pacing therapy delivered at block 620.

In one embodiment of the invention, the next combipolar pacing pulse is administered for a duration long enough to cause a ventricular extra-systole. In at least some embodiments of the invention, a ventricular action is initiated after a 600 ms duration. Other possible ranges of duration include, but are not limited to 200 to 1000 ms, 300 to 900 ms, 400 to 800 ms, 500 to 700 ms and 550 to 650 ms.

At block 645, the number of combipolar pacing therapies delivered is calculated. Generally, only a limited number of combipolar pacing therapies may be applied to cause ventricular extra-systole. Moreover, administration of combipolar pacing therapies may generally be successful in termination of atrial fibrillation after the first, second or third delivery. Thus, at block 645, it is determined if the number of combipolar pacing therapies delivered exceeds a particular limit. For example, the limit may be x number of combipolar pacing therapies. In one embodiment of the invention, x may equal any suitable number for ensuring optimal therapeutic benefit to the patient including, but not limited to a maximum of 4 combipolar therapies, 3 combipolar therapies and 2 combipolar therapies.

If the number of combipolar therapies delivered does not exceed the limit set at block 645, the method may proceed to block 635 as indicated by the loop at 647. At block 635, it may again be determined whether atrial fibrillation is occurring. This may be determined using any suitable method known in the arts or described above. If atrial fibrillation is no longer detected, the method returns to block 610 and the heart is paced at its regular pacing function. Alternatively, the heart may be paced at any suitable value once atrial fibrillation has been terminated. Before or while the heart returns to ordinary pacing function, data regarding the number of combipolar pacing therapies administered and the efficacy of the therapies administered may be stored for later retrieval and evaluation at block 650. This data may be stored, for example, in a storage location of IMD 10, including but not limited to, a location of memory 59 and/or RAM 68.

If atrial fibrillation is still detected, the method may proceed to block 640, when a next combipolar pacing therapy is delivered to the ventricle. The loop indicated at 647 may be repeated until administration of combipolar pacing therapy effectively terminates atrial fibrillation or until the limit of combipolar pacing therapies indicated at block 645 is exceeded.

At block 645, when the limit of combipolar pacing therapies has been exceeded, the method may return to block 610 and the heart is paced at its regular pacing function. Alternatively, the heart may be paced at any suitable value once atrial fibrillation has been terminated. Before or while the heart returns to ordinary pacing function, data regarding the number of combipolar pacing therapies administered and the efficacy of the therapies administered may be stored for later retrieval and evaluation at block 650. This data may be stored, for example, in a storage location of IMD 10, including but not limited to, a location of memory 59 and/or RAM 68.

Figure 7:
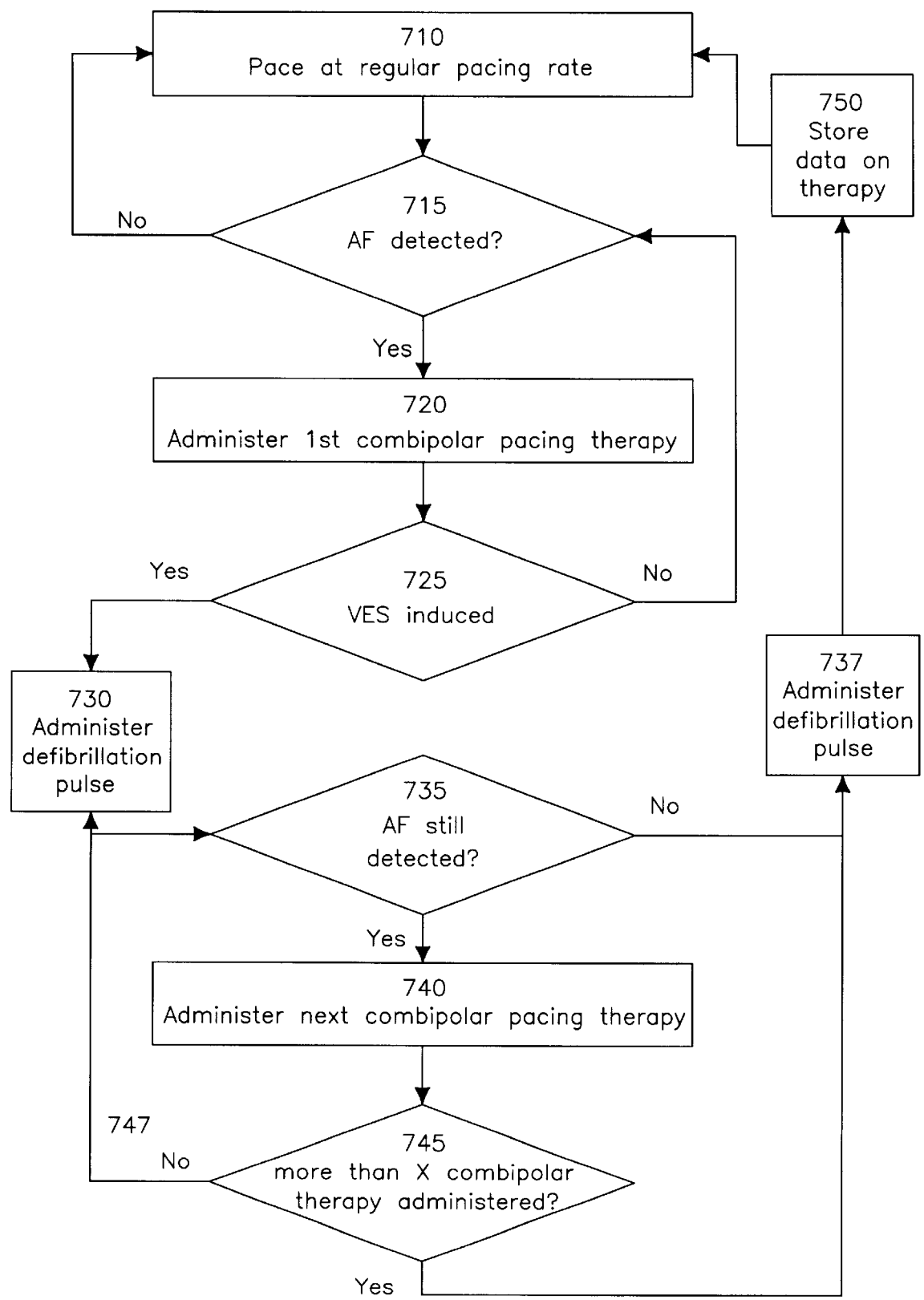
FIG. 7 is a flow diagram of another embodiment of a method for terminating atrial fibrillation in accordance with the present invention.

FIG. 7 illustrates one embodiment of a method for terminating atrial fibrillation in accordance with the present invention. As discussed above, the method of the present invention may be performed under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

At block 710, the cardiac tissue is paced at a regular pacing function. In one embodiment of the invention, the regular pacing function comprises pacing in a non-combipolar pacing fashion. Regular pacing function may be determined and set by a physician, may be based on the patient's medical history, may be a preprogrammed pacing function, may be selected from a look-up table or database, or calculated based on data gathered by IMD 10. Thus, at block 610, the right atrium may be paced by an electrode located within the right atrium, for example, atrial electrode 9, 13. Alternatively, the left atrium may be paced by an electrode located within the left atrium, for example, atrial electrode 9, 13. Meanwhile, the right ventricle may be paced by an electrode located within the right ventricle, for example, ventricular electrode 2, 3. Alternatively, the left ventricle may be paced by an electrode located within the left ventricle, for example, ventricular electrode 2, 3.

At block 715, it may be determined whether atrial fibrillation is detected. This may be determined using any suitable method known in the arts. For example, the sensing of a premature atrial contraction (PAC) or a premature ventricular contraction (PVC) is known in the art to indicate that atrial fibrillation is occurring. The PAC/PVC may be sensed, for example, by one or more of the sensing leads described above or by activity sensor 11. The occurrence of atrial fibrillation may be determined, for example, by an appropriate computer algorithm stored in memory or a portion of memory of microcomputer 58 of IMD 10. This determination may also be made as described above and illustrated in FIGS. 8–10. If no atrial fibrillation is detected, the method returns to block 710 and the heart is paced at its regular pacing function. Alternatively, the heart may be paced at any suitable value if no atrial fibrillation occurs.

If atrial fibrillation is detected, the method may proceed to block 720, when a first combipolar pacing therapy is delivered to the ventricle. This may take the form of, for example, a single combipolar pacing pulse. Combipolar pacing may be accomplished using any suitable method known in the arts. In one embodiment, leads 16 and 18 described above may be adapted to administer combipolar pacing pulses to cardiac tissue. For example, lead 16 may be adapted to administer pacing pulses as an atrial lead and lead 18 may be adapted to administer pacing pulses as a ventricular lead, or vice versa. Thus, lead 16 and lead 18 may administer a combipolar pulse by pacing at least one of the ventricles simultaneously. In at least some embodiments of the invention, a combipolar pulse may also be delivered in an alternating fashion, for example, the ventricle may be paced with lead 16 and immediately after with lead 18 or with lead 18 followed by lead 16. In some embodiments of the invention, combipolar pacing is preferably administered to the right ventricle. Alternatively a combipolar pacing pulse may be administered to an area of the right ventricle which bypasses right ventricle outflow tracks. Alternatively, a combipolar pacing pulse may be administered to the apex of the right ventricular sinus.

Alternatively, at least one of ventricular electrodes 2, 3 is used in a combipolar pacing fashion to induce a ventricular extra-systole in conjunction with at least one of the atrial electrodes 9, 13. Thus ventricular electrode 2,3 and atrial electrode 9, 13 may administer a combipolar pulse by pacing at least one of the ventricles simultaneously. In at least some embodiments of the invention, a combipolar pulse may also be delivered in an alternating fashion, for example, the ventricle may be paced with ventricular electrode 2,3 and then with atrial electrodes 9, 13 or vice versa, i.e., with atrial electrodes 9, 13 followed by ventricular electrodes 2, 3. In some embodiments of the invention, combipolar pacing is preferably administered to the right ventricle. Alternatively a combipolar pacing pulse may be administered to an area of the right ventricle which bypasses right ventricle outflow tracks. Alternatively, a combipolar pacing pulse may be administered to the apex of the right ventricular sinus.

In another embodiment of the invention ring electrode 2 may be adapted to administer pacing pulses as an atrial lead and coil electrode 5 may be adapted to administer pacing pulses as a ventricular lead, or vice versa. Thus, electrode 2 and electrode 5 may administer a combipolar pulse by pacing at least one of the ventricles simultaneously. In at least some embodiments of the invention, a combipolar pulse may also be delivered in an alternating fashion, for example, the ventricle may be paced with electrode 2 followed by electrode 5 or vice versa, i.e., the ventricle may be paced with electrode 5 followed by electrode 2. In some embodiments of the invention, combipolar pacing is preferably administered to the right ventricle. Alternatively a combipolar pacing pulse may be administered to an area of the right ventricle which bypasses right ventricle outflow tracks. Alternatively, a combipolar pacing pulse may be administered to the apex of the right ventricular sinus.

In one embodiment of the invention, circuitry 63 may be used to administer a combipolar pacing pulse by controlling pulses delivered from one or more electrodes.

The combipolar pacing therapy preferably delivers an effective amount of energy sufficient to terminate atrial fibrillation. The combipolar pacing may create a field in the area between the atrial and the ventricular leads. This field may cause the paces delivered by one or more of the atrial and/or ventricular leads to have a higher than normal amplitude or pulse width. Alternatively, a low energy pulse may be delivered from the combination of atrial and ventricular electrodes. In one embodiment of the invention, each of the electrodes delivers the maximum energy it is capable of delivering during administration of its first combipolar pacing pulse. Alternatively, a combination of low and high energy pulses may be administered as a first combipolar pacing pulse. In one embodiment of the invention, the first combipolar pacing pulse is administered for a duration long enough to cause a ventricular extra-systole. In at least some embodiments of the invention, a ventricular action is initiated after a 600 ms duration. Other possible ranges of duration include, but are not limited to 200 to 1000 ms, 300 to 900 ms, 400 to 800 ms, 500 to 700 ms and 550 to 650 ms.

At block 725, it may be determined if a ventricular extra-systole has been induced. The ventricular extra-systole may be sensed with any of the sensing electrodes described above. In one embodiment of the invention, the ventricular extra-systole is induced by the combipolar pacing of block 720. Detection of a ventricular extra-systole may be accomplished using any suitable method known in the arts. In one embodiment, one or more of sensing leads 16 and 18 and/or activity sensor 11 described above may be adapted to sense a ventricular extra-systole. Alternatively, at least one of ventricular electrodes 2, 3 may sense the ventricular extra-systole. In one embodiment of the invention, circuitry 63 may be used to determine if a ventricular extra-systole has been sensed.

In one embodiment of the invention, the ventricular extra-systole will have a interval shorter than the ordinary ventricular interval of the patient. This ordinary interval may be determined and set by a physician, may be based on the patient's medical history, may be a preprogrammed pacing interval, may be selected from a look-up table or database, or calculated based on data gathered by IMD 10.

In at least some embodiments of the invention, IMD 10 may determine the given interval of the first two or more detected atrial arrhythmia beats and will trigger delivery of the first combipolar pacing therapy so that it is administered on at a point in time which corresponds to the determined interval minus a selectable percentage of the determined interval, i.e., $$\text{time of combipolar pacing interval} = \text{determined interval} - \text{percentage of determined interval}$$

This percentage may be based on the vulnerable phase of the T-wave. The T-wave phase may be sensed, for example using sensor 11 or the sensing electrodes described above. Alternatively, the percentage may be calculated from a programmable dynamic refractory period. This calculation may be accomplished, for example under the control of any appropriate computer algorithm stored in a memory or a portion of a memory of microcomputer 58 in IMD 10. Such a computer algorithm may be any program capable of being stored in an electronic medium such as, by way of example only, RAM 68 or ROM 70 of IMD 10, where the contents of RAM 68 and ROM 70 may be accessed and consequently executed by microprocessor 64/microcomputer 58.

If a not induced ventricular action is detected with the desired predetermined ordinary interval, a ventricular extra-systole may have occurred and the method may proceed to the optional step indicated at block 730. If a ventricular action is detected with an interval shorter than the predetermined ordinary interval concurrently succeeded by one or more ventricular actions with intervals equal to or shorter than the predetermined ordinary interval, a ventricular-couplet or run may have occurred and the method may proceed to the optional step indicated at block 730. Alternatively, the method may proceed to block 735.

The optional step indicated at block 730 may be used to help curb any possible ventricular fibrillation that may result from the administration of the combipolar pacing therapy. Thus, at block 730, a defibrillation pulse may be administered to the ventricle following combipolar pacing. For example ventricular electrodes 2, 3 may be used to administer pacing pulses to the ventricle affected by the combipolar pacing therapy. In a preferred alternative, defibrillation electrode 5 is used to administer defibrillation pulses to the ventricle affected by the combipolar pacing therapy. Once the defibrillation pulse(s) have been administered, the method may proceed to block 735.

At block 735, it may again be determined whether atrial fibrillation is occurring. This may be determined using any suitable method known in the arts. For example, the sensing of a premature atrial contraction (PAC) or a premature ventricular contraction (PVC) is known in the art to indicate that atrial fibrillation is occurring. The PAC/PVC may be sensed, for example, by one or more of the sensing leads described above or by activity sensor 11. The occurrence of atrial fibrillation may be determined, for example, by an appropriate computer algorithm stored in memory or a portion of memory of microcomputer 58 of IMD 10. If atrial fibrillation is no longer detected, the method returns to block 710 and the heart is paced at its regular pacing function. Alternatively, the heart may be paced at any suitable value once atrial fibrillation has been terminated. Before or while the heart returns to ordinary pacing function, data regarding the number of combipolar pacing therapies administered and the efficacy of the therapies administered may be stored for later retrieval and evaluation at block 750. This data may be stored, for example, in a storage location of IMD 10, including but not limited to, a location of memory 59 and/or RAM 68.

At block 735, determination if atrial fibrillation is still occurring may be made using the methods described above and illustrated in Graphs A–C, i.e., detecting an atrial arrhythmia that may indicate the onset of atrial fibrillation, detecting an atrial arrhythmia with an interval shorter than an predetermined interval established for the patient, detecting a plurality of atrial arrhythmias, and/or measuring the intervals of a plurality of atrial arrhythmias. In another embodiment of the invention, IMD 10 may redetect the atrium and re-tune to the existing cycle length. IMD 10 may then evaluate whether the existing cycle length represents atrial arrhythmia.

If atrial fibrillation is still detected, the method may proceed to block 740, when a next combipolar pacing therapy is delivered to the ventricle. This make take the form of, for example, a single combipolar pacing pulse. Combipolar pacing may be accomplished using any suitable method known in the arts. Combipolar pacing may be accomplished as described above using leads 16 and 18, ventricular electrodes 2, 3 and atrial electrodes 9, 13, or using ring electrode 2 and coil electrode 5.

In one embodiment of the invention, circuitry 63 may be used to administer a combipolar pacing pulse by controlling pulses delivered from one or more electrodes.

The combipolar pacing therapy preferably delivers an effective amount of energy sufficient to terminate atrial fibrillation. The combipolar pacing may create a field in the area between the atrial and the ventricular leads. This field may cause the paces delivered by one or more of the atrial and/or ventricular leads to have a higher than normal amplitude or pulse width. Alternatively, a low energy pulse may be delivered from the combination of atrial and ventricular electrodes. In one embodiment of the invention, each of the electrodes delivers the maximum energy it is capable of delivering during administration of its first combipolar pacing pulse. Alternatively, a combination of low and high energy pulses may be administered as a first combipolar pacing pulse. In one embodiment of the invention, the first combipolar pacing pulse is administered for a duration long enough to cause a ventricular extra-systole. In at least some embodiments of the invention, a ventricular action is initiated after a 600 ms duration. Other possible ranges of duration include, but are not limited to 200 to 1000 ms, 300 to 900 ms, 400 to 800 ms, 500 to 700 ms and 550 to 650 ms.

At block 745, the number of combipolar pacing therapies delivered is calculated. Generally, only a limited number of combipolar pacing therapies may be applied to cause ventricular extra-systole. Moreover, administration of combipolar pacing therapies may generally be successful in termination of atrial fibrillation after the first, second or third delivery. Thus, at block 745, it is determined if the number of combipolar pacing therapies delivered exceeds a particular limit. For example, the limit may be x number of combipolar pacing therapies. In one embodiment of the invention, x may equal any suitable number for ensuring optimal therapeutic benefit to the patient including, but not limited to a maximum of 4 combipolar therapies, 3 combipolar therapies and 2 combipolar therapies.

If the number of combipolar therapies delivered does not exceed the limit set at block 745, the method may proceed to the optional step indicated at block 730 or to block 735 as indicated by the loop at 747. The optional step indicated at 730 may be used to help curb any possible ventricular fibrillation that may result from the administration of the combipolar pacing therapy. Thus, at block 730, a defibrillation pulse or pulses may be administered to the ventricle following combipolar pacing.

Alternatively, at block 735, it may again be determined whether atrial fibrillation is occurring. This may be determined using any suitable method known in the arts or described above. If atrial fibrillation is no longer detected, the method returns to block 710 and the heart is paced at its regular pacing function. Alternatively, the heart may be paced at any suitable value once atrial fibrillation has been terminated. Before or while the heart returns to ordinary pacing function, data regarding the number of combipolar pacing therapies administered and the efficacy of the therapies administered may be stored for later retrieval and evaluation at block 750. This data may be stored, for example, in a storage location of IMD 10, including but not limited to, a location of memory 59 and/or RAM 68.

In some embodiments of the invention, an optional step as indicated at block 737 may include administering a defibrillation pulse or pulses before the method returns to block 710. The optional step indicated at 737 may be used to help curb any possible ventricular fibrillation that may result from the administration of the combipolar pacing therapy. Thus, at block 737, a defibrillation pulse may be administered to the ventricle following combipolar pacing.

If atrial fibrillation is still detected, the method may proceed to block 740, when a next combipolar pacing therapy is delivered to the ventricle. The loop indicated at 747 may be repeated until administration of combipolar pacing therapy effectively terminates atrial fibrillation or until the limit of combipolar pacing therapies indicated at block 745 is exceeded.

At block 745, when the limit of combipolar pacing therapies has been exceeded, the method may return to block 710 and the heart is paced at its regular pacing function. Alternatively, the heart may be paced at any suitable value once atrial fibrillation has been terminated. Before or while the heart returns to ordinary pacing function, data regarding the number of combipolar pacing therapies administered and the efficacy of the therapies administered may be stored for later retrieval and evaluation at block 650. This data may be stored, for example, in a storage location of IMD 10, including but not limited to, a location of memory 59 and/or RAM 68.

In some embodiments of the invention, an optional step as indicated at block 737 follows block 746. This optional step may include administering a defibrillation pulse or pulses before the method returns to block 710. The optional step indicated at 737 may be used to help curb any possible ventricular fibrillation that may result from the administration of the combipolar pacing therapy. Thus, at block 737, a defibrillation pulse may be administered to the ventricle following combipolar pacing.

In the embodiments of the invention seen in FIGS. 6 and 7, the parameters determined include: initial pacing function value, combipolar pacing function value, detection of ventricular extra-systole, and duration of combipolar pacing. One or any suitable combination of these parameters may be varied in accordance with the present invention. Alternatively, one or more of these parameters may be set at a desired value while one or more other parameters are varied in accordance with the present invention. Moreover, although the parameters are shown as being determined in a given order, these parameters may be determined in any combination and in any order in accordance with the present invention.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for increasing a pacing parameter of a mammalian heart. The present invention is also not limited to the termination of atrial fibrillation or the induction of ventricular extra-systole, per se, but may find further application as a means of administering pacing therapy. The present invention further includes within its scope methods of making and using the measurement means described hereinabove.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

I claim:

1. A method of pacing cardiac tissue using an implantable medical device, comprising:

detecting atrial fibrillation in cardiac tissue;

pacing an area of the cardiac tissue via an atrial electrode and a ventricular electrode;

simultaneously pacing the area of the cardiac tissue via a pair of ventricular electrodes;

determining whether ventricular extra-systole is induced; and continuing the simultaneous pacing until ventricular extra-systole is induced.

2. The method of claim 1 further comprising:

adjusting a rate at which the area of the cardiac tissue is paced via the at least one atrial electrode.

3. The method of claim 1 further comprising:

adjusting a rate at which the area of the cardiac tissue is paced via the pair of ventricular electrodes.

4. The method of claim 1 further comprising:

stopping pacing of the area of cardiac tissue with the atrial electrode once the ventricular extra-systole is determined to be induced.

5. The method of claim 1 further comprising:

stopping pacing of the area of cardiac tissue with the pair of ventricular electrodes once the ventricular extra-systole is determined to be induced.

6. An implantable medical system, comprising:

means for detecting atrial fibrillation in the cardiac tissue;

means for pacing an area of the cardiac tissue via an atrial electrode and a ventricular electrode;

means for simultaneously pacing the area of the cardiac tissue via a pair of ventricular electrodes; and means for determining whether ventricular extra-systole is induced.

7. The system of claim 6 further comprising:

means for adjusting a rate at which the area of the cardiac tissue is paced via the atrial electrode.

8. The system of claim 6 further comprising:

means for adjusting a rate at which the area of the cardiac tissue is paced via the pair of ventricular electrodes.

9. The system of claim 6 further comprising:

means for stopping pacing of the area of cardiac tissue via the atrial electrode once the ventricular extra-systole is determined to be induced.

10. The system of claim 6 further comprising:

means for stopping pacing of the area of cardiac tissue via the pair of ventricular electrodes once the ventricular extra-systole is determined to be induced.

11. A computer usable medium including a program for pacing cardiac, comprising:

computer program code that detects atrial fibrillation in the cardiac tissue;

computer program code that paces an area of the cardiac tissue via an atrial electrode and a ventricular electrode;

computer program code that simultaneously paces the area of the cardiac tissue via a pair of ventricular electrodes;

computer program code that determines whether ventricular extra-systole is induced; and computer program code that continues the pacing until ventricular extra-systole is induced.

* * * * *

UNITED STATES PATENT AND TRADEMARK OFFICE
CERTIFICATE OF CORRECTION

| | | |
|---|---|---|
| PATENT NO. | : 6,813,518 B2 | Page 1 of 1 |
| APPLICATION NO. | : 09/846769 | |
| DATED | : November 2, 2004 | |
| INVENTOR(S) | : Bernhard Kupper | |

It is certified that error appears in the above-identified patent and that said Letters Patent is hereby corrected as shown below:

Column 21, line 32, please delete "Graphs A-C" and insert --Figs. 8-10--

Signed and Sealed this

Nineteenth Day of December, 2006

JON W. DUDAS
*Director of the United States Patent and Trademark Office*